United States Patent
Marijnissen et al.

[11] Patent Number: 6,011,621
[45] Date of Patent: Jan. 4, 2000

[54] METHOD AND APPARATUS FOR MEASURING PARTICLE SIZE AT LOW CONCENTRATION

[75] Inventors: Johannes Cornelis Maria Marijnissen, Breda; Alexander Willem Willemse, Rotterdam, both of Netherlands; Rein André Roos, Nocé, France

[73] Assignee: Technische Universiteit Delft, Netherlands

[21] Appl. No.: 09/051,206

[22] PCT Filed: Oct. 4, 1996

[86] PCT No.: PCT/NL96/00388

§ 371 Date: Sep. 14, 1998

§ 102(e) Date: Sep. 14, 1998

[87] PCT Pub. No.: WO97/13139

PCT Pub. Date: Apr. 10, 1997

[30] Foreign Application Priority Data

Oct. 4, 1996 [NL] Netherlands ............ 1001369

[51] Int. Cl.[7] .................................. C01N 15/02
[52] U.S. Cl. ............................ 356/336; 356/338
[58] Field of Search ............. 356/336, 337, 356/338, 339, 28.5; 250/574

[56] References Cited

U.S. PATENT DOCUMENTS

| | | | |
|---|---|---|---|
| 4,762,413 | 8/1988 | Namba et al. | 356/339 |
| 4,828,388 | 5/1989 | Namba | 356/339 |
| 5,502,561 | 3/1996 | Hutchins et al. | 356/336 |
| 5,583,635 | 12/1996 | Miura et al. | 356/339 |

FOREIGN PATENT DOCUMENTS 0 359 681   3/1990   European Pat. Off. .

OTHER PUBLICATIONS

Drunen et al., "Measurement of Aerosols in a Silicon Nitride Flame by Optical Fiber Photon Correlation Spectroscopy", *J. Aerosol Sci.*, vol. 25, No. 5, 1994, pp. 895–908.

Weber et al., "Analysis of a Flowing Aerosol by Correlation Spectroscopy: Concentration, Aperture, Velocity and Particle Size Effects", *J. Aerosol Sci.*, vol. 24, No. 4, 1993, pp. 485–499.

*Primary Examiner*—Hoa Q. Pham
*Attorney, Agent, or Firm*—Michaelson & Wallace; Peter L. Michaelson

[57] ABSTRACT

Described is an improved method for measuring the particle size of ultrasmall particles (111) which are suspended in a fluid. Laser light (121) is scattered by the particles, and the scattered light (122) is received by a light detector (131) which provides an electrical measuring signal ($S_m$) which is representative of the intensity of the scattered light (122). According to the present invention, signal components with a relatively low characteristic frequency are removed from the electrical measuring signal ($S_m$), and the particle size is calculated on the basis of the thus corrected measuring signal ($S_c$), so that also at a very low concentration of the particles (111) reliable results are achieved.

15 Claims, 4 Drawing Sheets

METHOD AND APPARATUS FOR MEASURING PARTICLE SIZE AT LOW CONCENTRATION

BACKGROUND OF THE INVENTION

1. Field of the Invention

In the art, there is a need for a method for measuring the particle size of ultra-small particles which are suspended in a fluid. More particularly, this concerns particles whose size is typically in the range of 1–3000 nm, but the particles can also be smaller than 1 nm.

The particles can be liquid or solid.

Examples of fields of application where the above-mentioned need exists, are:

environmental technology: measurement of aerosols, for instance soot particles in air, asbestos particles in air.

biology: measurement of, for instance, virus particles in air, pollen in air.

production-technology: measurement of, for instance, dust particles in air in so-called "clean rooms"; production of ultra-fine particles in a gas or a liquid (for instance dyes or medicines).

medical analysis: measurement of body fluids, for instance blood composition, and the measurement of deposition of particles in the human body, in particular in the lungs.

2. Description of the Related Art

The need mentioned has existed for some time already, and measuring methods have already been developed to enable such measurements as mentioned to be carried out. An example of such a measuring method, known per se, is photon correlation spectroscopy, hereinafter designated as PCS. For an extensive description of this measurement technique, reference is made to the professional literature, such as, for instance, the article "Measurement of Aerosols in a Silicon Nitride Flame by Optical Fiber Photon Correlation Spectroscopy" by M. A. van Drunen et al in J. Aerosol Sci, 1994, vol. 25, no. 5, pp. 895–908. More particularly, in Chapter 2 of that article the theory underlying PCS is set out.

As explained in that article, PCS is based on the fact that particles suspended in a fluid undergo a Brownian movement, with the movement frequency of the particles being dependent (inter alia) on their size: the smaller the particles, the greater that frequency. A measuring signal representing that movement frequency can be derived from light which is reflected by the particles, more particularly from the fluctuations in the intensity of that light, which fluctuations, moved over a particular delay time, are correlated with themselves.

During the performance of a measurement, the measuring apparatus only "sees" a relatively small measuring volume, which is to say that only light signals from the particles present in that measuring volume are processed. In practice, that measuring volume typically has a magnitude of the order of $10^{-6}$ cm$^3$. The strength of the measuring signal, that is, the intensity of the light received from that measuring volume is dependent, inter alia, on the concentration of the particles and more particularly on the number of particles present in the measuring volume: the more particles are present in the measuring volume, the more particles contribute to the measuring signal, that is, the greater that intensity.

A problem presenting itself here is based on the fact that the particles have a kinetic energy, that is, a velocity dependent on the temperature, as a result of which some particles will leave the measuring volume while other particles will enter the measuring volume. As a consequence, the number of particles actually present in the measuring volume at a particular time will not be constant but fluctuate over time. This fluctuation in the number of particles causes a second intensity fluctuation in the measuring signal, which influences the measuring signal. This effect is negligible in the case of relatively large numbers of particles because then the fluctuation in the number of particles is negligible with respect to the total number of particles. At low concentrations, however, in particular when the number of particles in the measuring volume is less than about 200, a noticeable effect occurs, which is greater when the number of particles in the measuring volume is smaller. The influence on the measuring result is such that the measured size of the particles differs from the actual size; more particularly, the measured size is greater than the actual size. In consequence, it has been assumed heretofore that PCS is only useful in cases of sufficiently high particle concentrations, as has been noted in Chapter 1 of the above-mentioned article, with reference to the article "Analysis of a Flowing Aerosol by Correlation Spectroscopy: Concentration, Aperture, Velocity and Particle Size Effects" by R. Weber et al in J. Aerosol Sci., 1993, vol. 24, p.485.

BRIEF SUMMARY OF THE INVENTION

The object of the present invention is to break through this prejudice and to improve the known PCS method in such a manner that it has good utility also at very low concentrations and yields reliable, accurate results.

The present invention is based on the insight that although the above-mentioned fluctuations in the number of particles and the second intensity fluctuations in the measuring signal thereby caused are statistical phenomena, as are the first intensity fluctuations caused by the Brownian movement, those second fluctuations occur in a characteristic frequency range which is appreciably lower than the characteristic frequency range in which the first intensity fluctuations caused by the Brownian movement occur. Therefore, according to the present invention, it is possible to make a distinction between these two types of fluctuations.

Thus, according to a first aspect of the present invention, the calculation of the particle size is carried out solely on the basis of the first fluctuations.

Further, according to a second aspect of the present invention, a method is provided for calculating on the basis of the second fluctuations the particle concentration, more particularly the number of particles in the measuring volume.

BRIEF DESCRIPTION OF THE DRAWINGS

The present invention will be clarified by the following description of a preferred embodiment of a method and apparatus according to the invention, with reference to the drawings, wherein.

DETAILED DESCRIPTION

Figure 1:
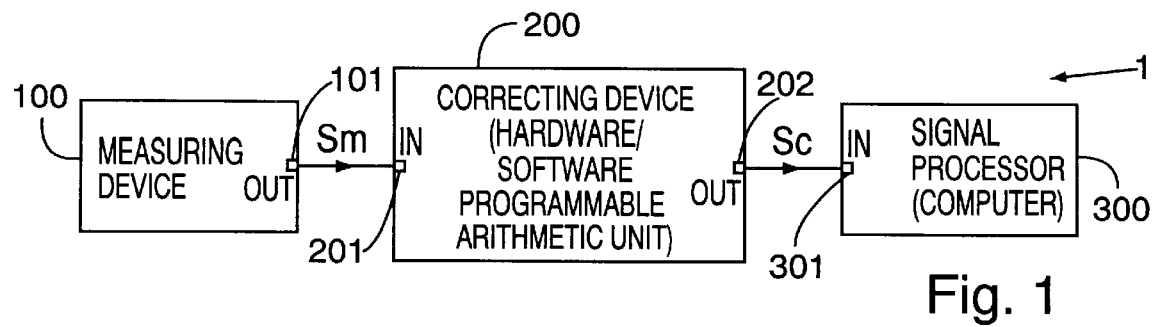
FIG. 1 shows a block diagram of an apparatus according to the invention.

With reference to FIG. 1, the structure of a measuring system 1 according to the invention will presently be explained in outline. The measuring system 1 comprises a measuring device 100 with an output 101 for supplying an electrical measuring signal $S_m$; a correcting device 200 with an input 201 for receiving the electrical measuring signal $S_m$, and an output 202 for supplying a corrected electrical measuring signal $S_c$; and a signal processing device 300 with an input 301 for receiving the corrected electrical measuring signal $S_c$.

Figure 2:
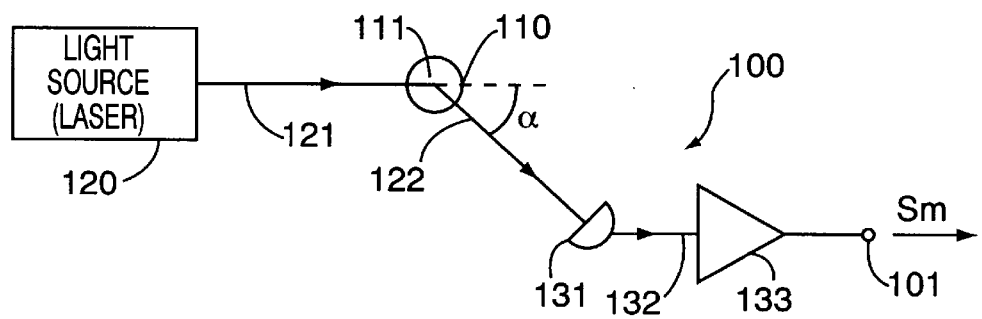
FIG. 2 shows a schematic overview of a measuring device used in the apparatus according to the invention.

In the measuring system 1 according to the present invention, the measuring device 100 and the signal processing device 300 can be conventional devices, as known in this technical field. In a conventional particle size measuring system, the correcting device 200 is absent, and the output 101 of the measuring device 100 is connected to the input 301 of the signal processing device 300. Although the nature and construction of the measuring device 100 and the signal processing device 300 do not constitute a subject of the present invention, and are known per se to a skilled person in this technical field, they will be briefly explained hereinafter with reference to FIGS. 2–4.

The measuring device 100 comprises a measuring chamber 110 accommodating a fluid having suspended therein the particles 111 to be examined. The measuring chamber 110 has walls which are transparent to light. The measuring device 100 further comprises a light source 120 for coherent light, such as, for instance, a laser. A light beam 121 generated by the laser light source 120 is directed to the measuring chamber 110, with means being present (not shown for simplicity's sake) for converging the laser beam 121 at a particular point within the measuring chamber 110.

The laser light beam 121 is scattered by the particles 111 in the measuring chamber 110, the extent of the scatter being dependent on the scattering angle $\alpha$. At a predetermined position, which is generally adjustable, a photosensitive detector 131 is arranged, which receives the light 122 which has been scattered at a predetermined scattering angle $\alpha$ and provides an electrical signal 132 which is proportional to the intensity of the received light 122. The electrical signal 132 is fed to an amplifier 133, which supplies the electrical measuring signal $S_m$ at its 101 output. It is noted that the detector 131 and the amplifier 133 can be constructed as one whole. Preferably, the detector 131 comprises a photomultiplier tube.

The detector 131 is arranged to receive only those light signals that originate from a limited solid angle, which is designated as the field of view of the detector 131. The section of the field of view of the detector 131 and the area of convergence of the laser beam 121 is designated as the measuring volume. The intensity of the scattered light 122 is dependent inter alia on the number of particles in that measuring volume.

Each particle in the measuring volume scatters the incoming light 121 in a characteristic way and generates a spatial pattern of scattered light. If at least two particles are in the measuring volume, the scattered light patterns caused by those particles will interfere with each other. As a result of the Brownian movement of the particles, the interference patterns will vary in a random, statistically determined manner. This is manifest in the intensity of the scattered light 122 through a fluctuation in the intensity, as schematically represented in FIG. 3, where time t is plotted horizontally in arbitrary units (a.u.) and the intensity I is plotted vertically in arbitrary units (a.u.).

These intensity fluctuations are representative of the diffusion coefficient of the particles in the medium, which in turn is dependent inter alia on the size of the particles the signal processing device 300 comprises a suitably programmed computer which, taking into account parameters such as the temperature, viscosity of the fluid, etc., calculates from the fluctuations in the signal received at its input 301 the diffusion coefficient and/or the particle size and reproduces them, for instance in the form of a graph and/or printed numbers. An example of a conventional signal processing device 300 is based on the performance of an auto-correlation technique, whereby, briefly stated, it is determined on what time scale an averaging of the signal received at the input 301 yields a constant value. A small time scale then corresponds with small particles.

Figure 3:
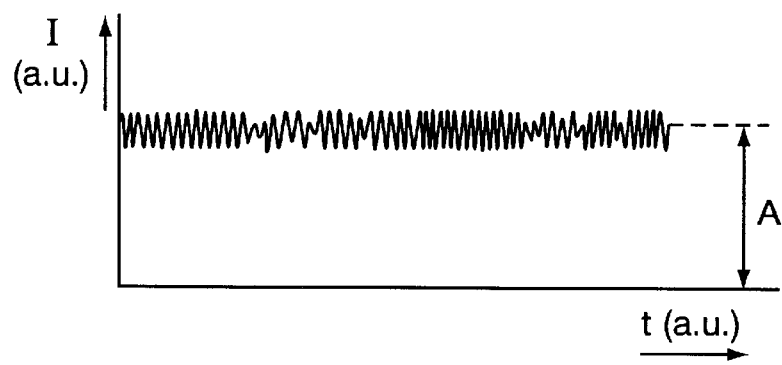
FIG. 3 shows a graph which is representative of a measuring signal obtained with the measuring device shown in FIG. 2.

In FIG. 3 it is shown that the fluctuations referred to occur around an average level designated A, which level is dependent on the number of particles in the measuring volume. The conventional signal processing device 300 has proved to give good results if the signal received at its input 301 does indeed have the shape represented in FIG. 3, which occurs if the concentration of the particles in the fluid is sufficiently high, more particularly if the number of particles in the measuring volume is sufficiently large.

In principle, the number of particles in the measuring volume is not constant, since owing to the kinetic energy of the particles, particles will leave the measuring volume while other particles will enter the measuring volume. As mentioned, the intensity of the scattered light 122 is dependent inter alia on the number of particles in the measuring volume, so that the above-mentioned fluctuation in the number of particles will cause an intensity fluctuation.

If the number of particles in the measuring volume is sufficiently large, this effect is negligible, and the number of particles in the measuring volume may be regarded as being constant over time. More particularly, in that case the average intensity level A may be regarded as being constant over time, in which case the conventional signal processing device 300, as mentioned, yields good results.

Figure 4:
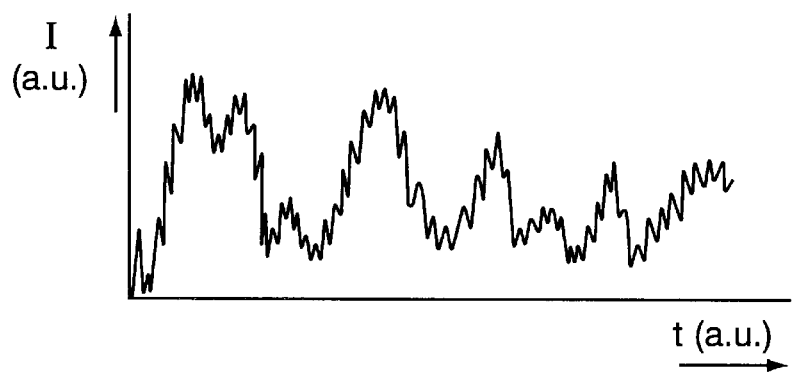
FIG. 4 shows a graph similar to FIG. 3 in a situation where the particle concentration is low.
Figure 5:
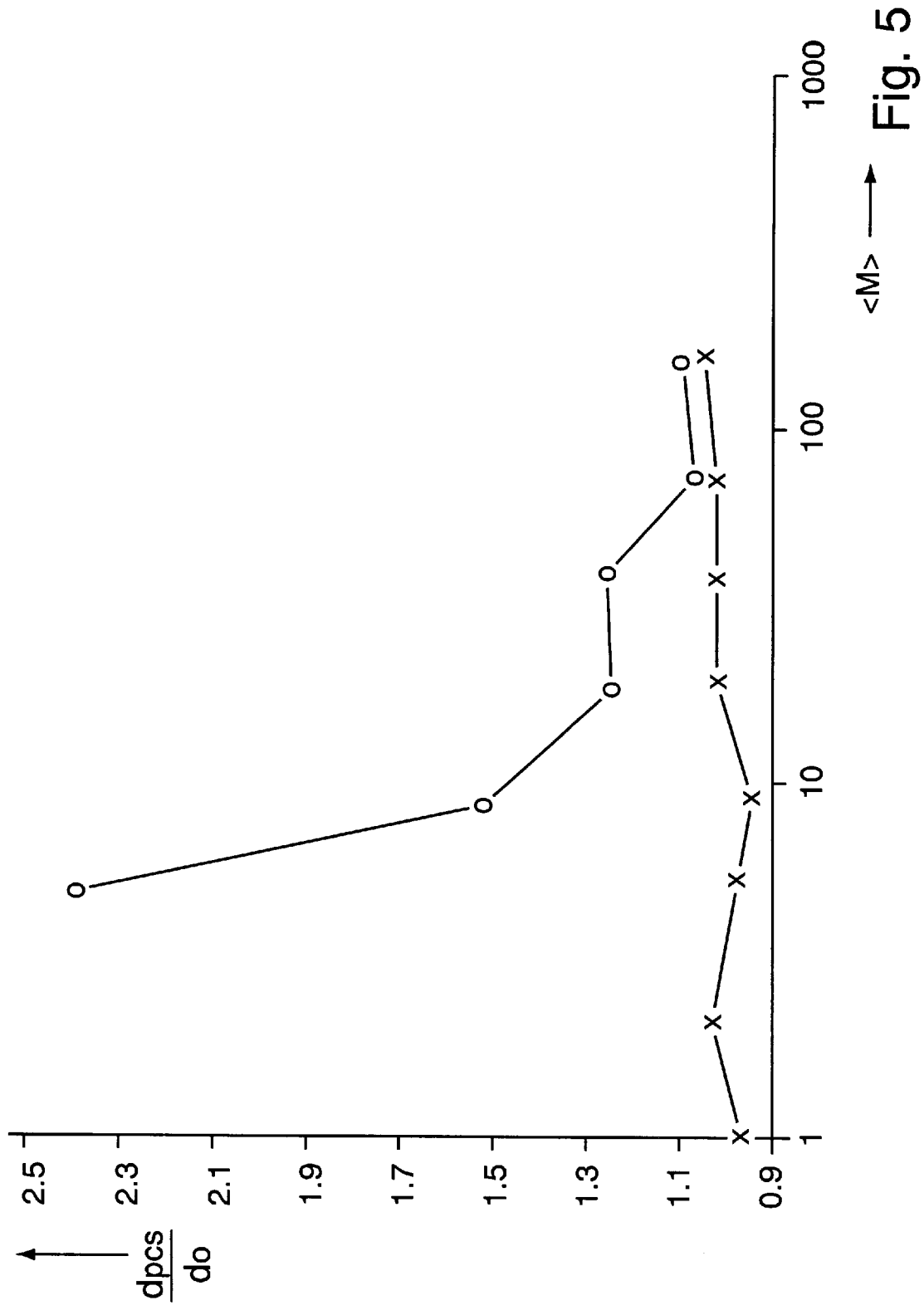
FIG. 5 is a graphic representation of a few measuring results.

However, if the number of particles in the measuring volume is not large enough, more particularly lower than about 100–200, the effect mentioned is no longer negligible, but manifests itself in a statistically determined fluctuation of the average intensity level A, as schematically illustrated in FIG. 4. In such cases the conventional signal processing device 300 can no longer yield good results. This is illustrated in the graph of FIG. 5, which shows the result of an experiment with latex particles of a size $d_0$ of 501 nm (on average), suspended in water with a temperature T=298 K and a viscosity $\eta$=0.8904 cP. The light source 120 used was an Argon Ion laser, and the laser light beam 121 had a wavelength $\lambda$=514.5 nm. The detector 131 was arranged at a scattering angle $\alpha$=75°. Plotted along the logarithmic horizontal axis is the average number of particles <M> in the measuring volume, as determined through calculation. Plotted along the vertical axis is the ratio between actual particle size $d_0$ and the calculated particle size $d_{pcs}$ calculated by the conventional signal processing device 300. Measuring points indicated by a circle (o) correspond with the results obtained when the signal input 301 of the conventional signal processing device 300 was connected to the signal output 101 of the measuring device 100. It is clear to see in FIG. 5 that when the number of particles in the measuring volume is lower, the value of the measured or calculated particle size value $d_{pcs}$ deviates more from the real value $d_0$.

As appears from FIG. 4, the above-mentioned fluctuation of the average intensity level A occurs with a time scale that is greater than the time scale corresponding with fluctuations in the interference patterns caused by the Brownian movement, which is "interpreted" by the conventional signal processing device 300 as a greater particle size. This implies that the conventional measuring system is then no longer useful for supplying reliable results. From FIG. 5 it appears that in the example described, the conventional measuring system no longer yields reliable results for values of <M> less than about 100. At values of <M> less than about 5 it was even found to be entirely impossible to obtain meaningful measuring results.

A complicating factor in this connection is that the user of the conventional measuring system does not know whether the measuring result provided is reliable or not. To be able to make any pronouncements about that, the user should have information about the number of particles in the measuring volume, that is, about the concentration of the particles, for which purpose a separate measurement with separate measuring apparatus is required.

Surprisingly, it has been found according to the present invention that it is possible with relatively simple means to correct for the influence of the fluctuations in the number of particles. It has been found that in spite of the fact that the particle number fluctuations are statistically determined, as are the fluctuations in the interference patterns caused by the Brownian movement, the particle number fluctuations typically occur on a time scale with a considerably greater time constant than do the fluctuations caused by the Brownian movement. According to the present invention, the two contributions are separable through relatively simple filtering techniques. To that end, according to the present invention, the correcting device 200 is connected between the measuring device 100 and the signal processing device 300 (see FIG. 1).

Figure 6:
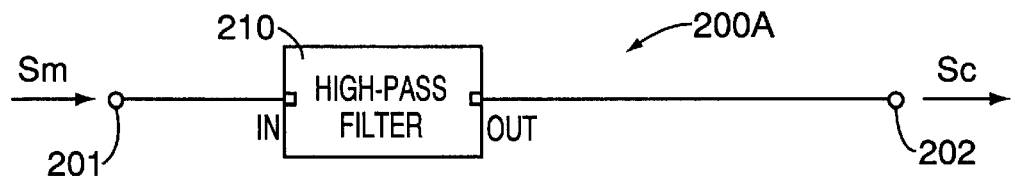
FIGS. 6–9 schematically show a few examples of a correcting device according to the present invention.

FIG. 6 shows a first embodiment of a correcting device 200 according to the present invention. In this simple embodiment the correcting device 200A comprises a high-pass filter 210 connected between the input 201 and the output 202. The high-pass filter 210, of which the slope is preferably as great as possible, has a suitably chosen crossover point or cut-off frequency, such that the signal components of relatively low frequency, deriving from the particle number fluctuations, are stopped while the signal components of relatively high frequency, deriving from the fluctuations caused by the Brownian movement, are passed.

Figure 7:
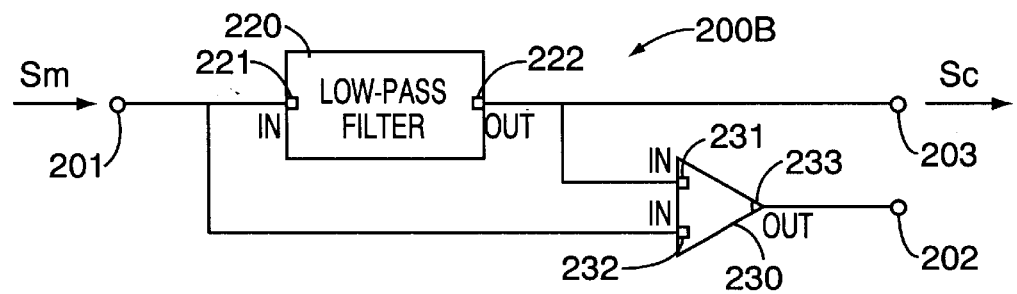

FIG. 7 shows a second embodiment of a correcting device 200B according to the present invention. In this second embodiment the correcting device 200 comprises a low-pass filter 220, of which an input 221 is connected to the input 201 of the correcting device 200B, and a differential amplifier 230, of which a first input 231 is connected to an output 222 of the low-pass filter 220. A second input 232 of the differential amplifier 230 is connected to the input 201 of the correcting device 200B. An output 233 of the differential amplifier 230 is connected to the output 202 of the correcting device 200B. The low-pass filter 220 has a suitably chosen crossover point or cut-off frequency, such that the signal components of relatively low frequency, deriving from the fluctuations in the number of particles, are transmitted while the signal components of relatively high frequency, deriving from the fluctuations caused by the Brownian movement, are retained, Thus the low-pass filter 220 provides at its output 222 a signal that is representative of the contribution to the measuring signal $S_m$ caused by the fluctuations in the number of particles, and the differential amplifier 230 removes that contribution from the measuring signal $S_m$.

An advantage of this second embodiment is that the signal provided at the output 222 of the low-pass filter 220 can be delivered to a second output 203 of the correcting device 200B as a signal which is indicative of the number of particles in the measuring volume and of the concentration of the particles in the measuring volume, respectively. Thus, according to the invention it is no longer necessary to provide separate measuring equipment for measuring the particle concentration, which constitutes an additional advantage of the invention.

Figure 8:
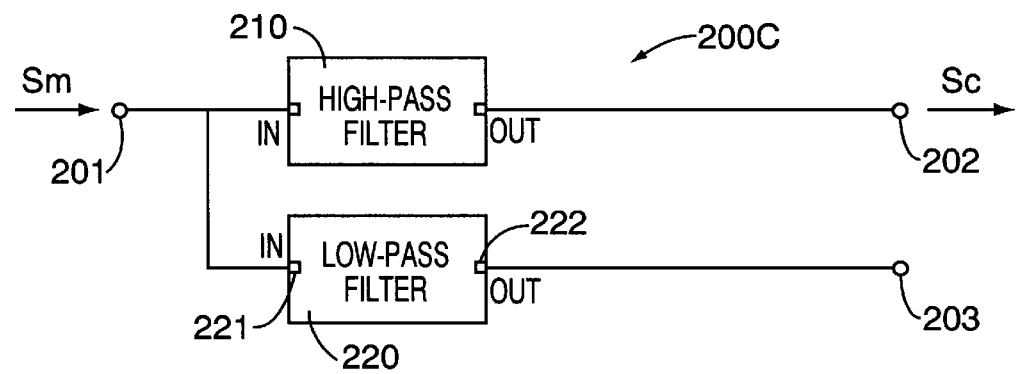

FIG. 8 shows a variant of the first embodiment of FIG. 6. Coupled parallel with the high-pass filter 210 is a low-pass filter 220 which, similarly to the low-pass filter 220 of FIG. 7, provides at a second output 203 of the correcting device 200C a signal which is indicative of the number of particles in the measuring volume and of the concentration of the particles in the measuring volume, respectively.

Figure 9:
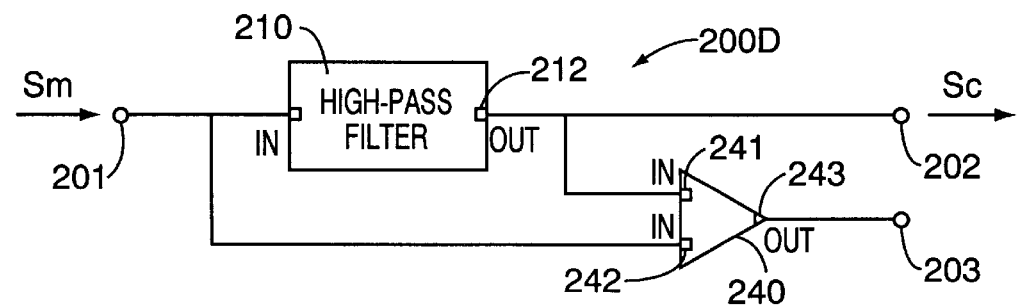

FIG. 9 shows another variant of the first embodiment of FIG. 6, which includes a differential amplifier 240, of which a first input 241 is connected to an output 212 of the high-pass filter 210. A second input 242 of the differential amplifier 240 is connected to the input 201 of the correcting device 200D. An output 243 of the differential amplifier 240 is connected to a second output 203 of the correcting device 200D. The high-pass filter 210 provides at its output 212 a signal which is representative of the contribution to the measuring signal $S_m$ caused by the Brownian movement, and the differential amplifier 240 removes that contribution from the measuring signal $S_m$, for providing at the second output 203 a signal which is representative of the contribution to the measuring signal $S_m$ caused by the particle number fluctuations, and which is thus indicative of the number of particles in the measuring volume and of the concentration of the particles in the measuring volume, respectively.

The effect of the measures proposed by the present invention can be illustrated with the aid of the graph of FIG. 5. Under the same conditions the experiment described in the foregoing was repeated, but now the correcting device 200B of FIG. 7 was coupled between the measuring device 100 and the signal processing device 300. The cut-off frequency of the low-pass filter 220 was set at 37 Hz, while the light intensity fluctuations caused by the Brownian movement of the particles 111 typically had a frequency of 384.4 Hz. The measuring points thus obtained with the measuring system 1 of FIG. 1 are indicated in FIG. 5 with a cross (x). It appears clearly from FIG. 5 that it is possible with the apparatus according to the invention to obtain reliable measuring results also in the case of very low values for <M>, even when the number of particles in the measuring volume is less than 5.

In the foregoing, it has been mentioned that the filters must have a suitably chosen crossover point or cut-off frequency (−3 dB point). That crossover point can be determined, for instance, experimentally, and be manually set by the user by setting appropriate values for some components of the filters, as will be clear to a skilled person. Such a relatively simple embodiment can be considered adequate in situations where the size of the particles will not change significantly.

Figure 10:
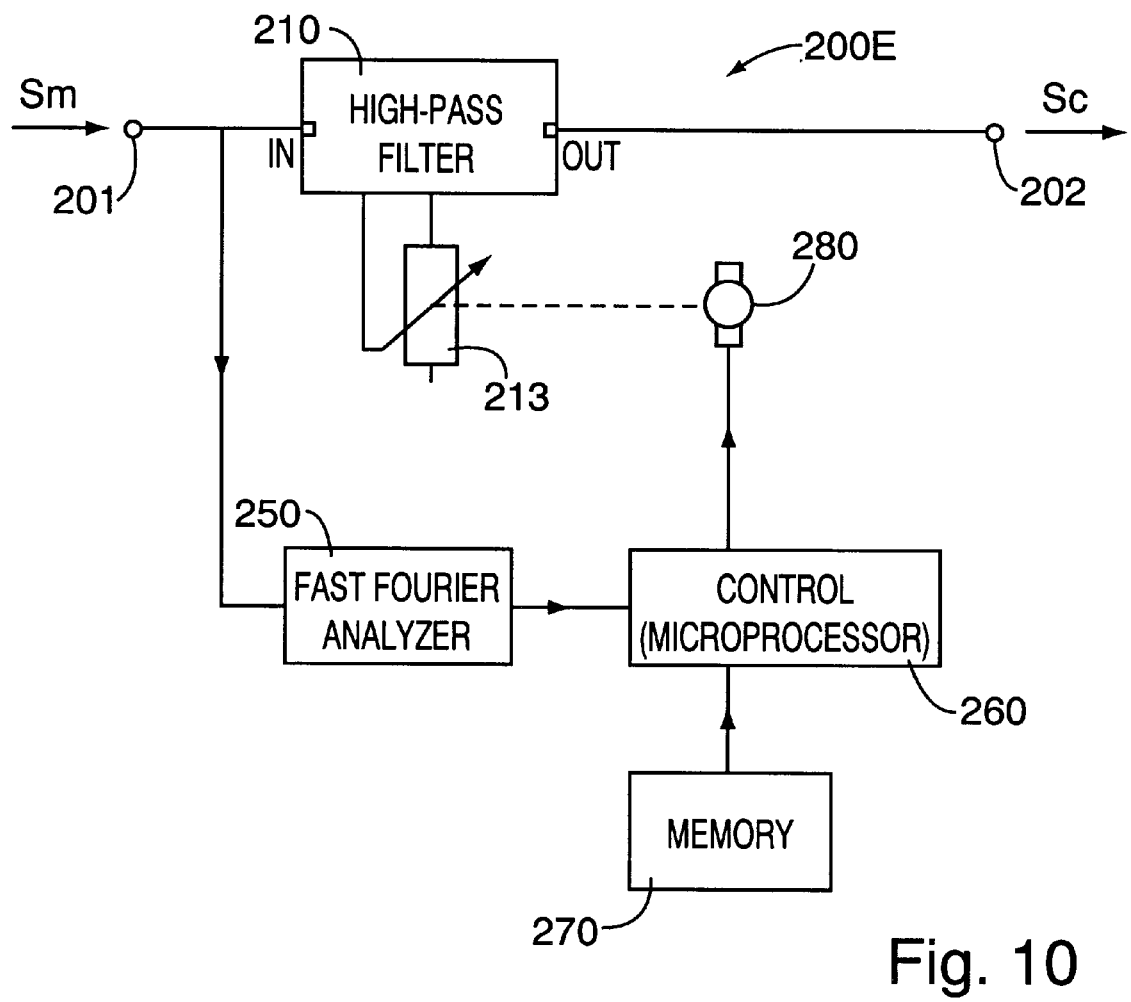
FIG. 10 schematically shows an example of a self-setting correcting device.

However, there are situations conceivable where the size of the particles is not constant. An example of such a situation concerns the instance where the particles will react with each other, whereby the number of particles will decrease while the size of the particles will increase. An example of such a situation is a sintering process or a coagulation process. In such situations it is preferred that the correcting device be self-adjusting. FIG. 10 illustrates an exemplary embodiment of such a self-adjusting correcting device 200E, which is based on the simple variant of the correcting device 200A illustrated in FIG. 6. It will be clear to a skilled person, however, that it is possible analogously to adapt the variants of FIGS. 7–9 to make the correcting device self-adjusting or adaptive.

FIG. 10 shows that the characteristic of the filter 210, in particular the cut-off frequency thereof, is adjustable by changing a value of a component thereof. Which component that is, depends on the type of filter chosen, as will be clear to a skilled person. In the example shown, the assumption is that that adjustable component is a variable resistance 213, whose slide can be displaced by means of a motor 280, under the control of a control device 260, which can comprise, for instance, a microprocessor.

The control device 260 receives in real time information about the frequency characteristic of the signal $S_m$. To that end, for instance a fast Fourier analyser 250 is connected to the input 201, which analyser 250 is connected to a data input of the control device 260. On the basis of the information received at this data input, the control device 260 decides at what frequency the crossover point of the filter 210 is to be set. From this, the control device 260 determines a setting for the variable resistance 213.

When setting the variable resistance 213, the control device 260 can set the position of the slide of the variable resistance 213. The control device 260 can calculate that setting position, or look it up in a memory 270, associated with the control device 260, in which memory there has been priorly stored a table of the relation between the setting point of the filter 210 and the setting position for the slide of the variable resistance 213. The motor 280 can be a stepping motor.

The control device 260 can also set the resistance of the variable resistance 213 directly. The control device 260 can calculate that setting resistance, or look it up in a memory 270, associated with the control device 260, in which memory there has been priorly stored a table of the relation between the setting point of the filter 210 and the setting resistance of the variable resistance 213. To be able to determine whether the instantaneous resistance corresponds with the resistance to be set, the variable resistance 213 can be of double design, with the position of the slide of the second variable resistance corresponding with the position of the slide of the first variable resistance, and with the slide of the second variable resistance being connected to a second data input of the control device 260. For simplicity's sake, this variant is not separately shown in FIG. 10.

It has been set out in the foregoing that the signal $S_m$ coming from the measuring device 100 can contain a disturbing signal component with a relatively low characteristic frequency, as a result of which calculations of the particle size are disturbed. Such a disturbing signal component is introduced when the number of particles in the measuring volume is relatively low, as a result of fluctuations in that particle number. In accordance with the present invention, by performing the calculations of the particle size exclusively on the basis of signal components of sufficiently high frequency, those calculations can be reliably performed at lower concentration than has been possible heretofore.

However, the invention also provides advantages in cases where such a disturbing signal component with a relatively low characteristic frequency is introduced into the signal $S_m$ coming from the measuring device 100 through a different cause. Also in the case of such different causes, the calculations would be disturbed, while through the use of the present invention the accuracy of the calculations is no longer dependent on such other causes. An example of such a different cause concerns the situation where owing to a rapid succession of pulses coming from the detector, these pulses start to overlap partly.

It will be clear to a skilled person that it is possible to change or modify the represented embodiment of the apparatus according to the invention without departing from the concept of the invention or the scope of protection as defined in the claims. It is possible, for instance, to realize the controllability of the transmission function of the correcting device 200 in a different way.

Also, it will be clear to a skilled person that the correction of the electrical measuring signal $S_m$ can be carried out with an electronic filter (hardware-wise), but that such a correction can also be carried out by means of a suitable arithmetic means (hardware- or software-wise). That arithmetic means can then be, for instance, an arithmetic unit of the signal processing device 300.

What is claimed is:

1. A method of measuring the particle size of ultra-small particles suspended in a fluid and experiencing Brownian movement, wherein the concentration of said ultra-small particles in said fluid is low, said method comprising the steps of:

irradiating a predetermined measuring volume of said ultra-small particles with a coherent beam of light to cause said light to be scattered by said ultra-small particles into a predetermined scattering angle;

detecting the intensity of said light scattered by said ultra-small particles in said predetermined scattering angle, wherein substantial variations in said intensity of said light are a function of said Brownian movement and fluctuations in the number of said ultra-small particles in said measuring volume;

generating an electrical measuring signal as a function of said intensity of said light scattered by said ultra-small particles;

removing from said electrical measuring signal first signal components with a relatively low characteristic frequency due substantially to said fluctuations in said number of said ultra-small particles in said measuring volume to produce a corrected signal representative of said Brownian movement and substantially free of variations due to said fluctuations in said number of said ultra-small particles in said measuring volume; and calculating from said corrected signal the size of said ultra-small particles.

2. The method of claim 1, wherein said calculating step includes performing an auto-correlation operation on said corrected signal.

3. The method of claim 1, wherein said removing step includes filtering from said electrical measuring signal said first signal components with said relatively low characteristic frequency, wherein said relatively low characteristic frequency is of a level to include variations caused by said fluctuations in said number of said ultra-small particles in said measuring volume, whereby said corrected signal includes only second signal components with a relatively high characteristic frequency substantially due to said Brownian movement.

4. The method of claim 1, wherein said removing step includes generating an auxiliary signal having said first signal components with said relatively low characteristic frequency, such that said auxiliary signal includes said first signal components representative of fluctuations in the number of said ultra-small particles in said measuring volume and substantially free of second signal components due to said Brownian movement.

5. The method of claim 4, wherein said removing step includes subtracting said auxiliary signal from said electrical measuring signal to produce said corrected signal.

6. The method of claim 4, wherein said calculating step includes calculating from said auxiliary signal the number and concentration of said ultra-small particles in said measuring volume.

7. A measuring system for measuring the size of ultra-small particles suspended in a fluid at low concentrations and experiencing Brownian movement in a predetermined measuring volume of said fluid, said measuring system comprising:

measuring means for generating an electrical measuring signal representative of the intensity of a light beam scattered by said ultra-light particles in said measuring volume along a predetermined scattering direction;

correcting means connected to said measuring means for receiving said electrical measuring signal and generating a corrected signal by removing from said electrical measuring signal first signal components of a relatively low characteristic frequency caused by fluctuations in the number of said ultra-small particles in said measuring volume, such that said corrected signal is a function of substantially only said Brownian movement of said ultra-small particles; and signal processing means connected to said correcting means for receiving said corrected signal and calculating therefrom the size of said ultra-small particles.

8. The measuring system of claim 7, wherein said correcting means comprises a high-pass filter having an input connected to said measuring means and an output connected to said signal processing means.

9. The measuring system of claim 8, further including a low-pass filter having an input connected to said measuring means and an output connected to said signal processing means.

10. The measuring system of claim 7, wherein said correcting means includes a programmable arithmetic means for filtering from said electrical measuring signal said first signal components caused by said fluctuations in the number of said ultra-small particles in said measuring volume.

11. A measuring system for measuring the size of ultra-small particles experiencing Brownian movement in a predetermined measuring volume comprising:

measuring means for generating an electrical measuring signal representative of the intensity of a light beam scattered by said ultra-light particles in a predetermined scattering direction;

correcting means connected to said measuring means for receiving said electrical measuring signal and generating a corrected signal by removing from said electrical measuring signal low-frequency components caused by fluctuations in the number of said ultra-small particles in said measuring volume, such that said corrected signal is substantially a function of said Brownian movement of said ultra-small particles, said correcting means comprising a low-pass filter having an input connected to said measuring means and an output, and a differential amplifier having a first input connected to said output of said low-pass filter, a second input connected to said measuring means and an output; and signal processing means connected to said output of said differential amplifier for receiving said corrected signal and calculating therefrom the size of said ultra-small particles.

12. The measuring system of claim 11, wherein said output of said low-pass filter connects to said signal processing means.

13. A measuring system for measuring the size of ultra-small particles experiencing Brownian movement in a predetermined measuring volume comprising:

measuring means for generating an electrical measuring signal representative of the intensity of a light beam scattered by said ultra-light particles in a predetermined scattering direction;

correcting means connected to said measuring means for receiving said electrical measuring signal and generating a corrected signal by removing from said electrical measuring signal low-frequency components caused by fluctuations in the number of said ultra-small particles in said measuring volume, such that said corrected signal is substantially a function of said Brownian movement of said ultra-small particles, said correcting means comprising a high-pass filter having an input connected to said measuring means and an output, and a differential amplifier having a first input connected to said output of said high-pass filter, a second input connected to said measuring means, and an output; and signal processing means connected to said output of said differential amplifier and to said output of said high-pass filter for receiving said corrected signal and calculating therefrom the size of said ultra-small particles.

14. A measuring system for measuring the particle size of ultra-small particles suspended in a fluid at low concentrations and experiencing Brownian movement comprising:

a measuring chamber containing said fluid with said ultra-small particles suspended therein;

a light source means for directing a beam of coherent light at said measuring chamber to illuminate a measuring volume of said fluid;

a light detector disposed at an angle with respect to said beam of coherent light to detect light scattered by said ultra-small particles;

a correcting device connected to said light detector, said correcting device comprising signal removal means for receiving from said light detector an electrical measuring signal of the intensity of said scattered light and removing from said electrical measuring signal first signal components with a relatively low characteristic frequency to produce a corrected signal substantially representative of said Brownian movement only and substantially free of variations due to fluctuations in the number of said ultra-small particles in said measuring volume; and a signal processor connected to said correcting device, said signal processor having means for calculating the size of said ultra-small particles.

15. The measuring system of claim 14, wherein said correcting device comprises a programmable arithmetic unit.

* * * * *